US007876910B2

(12) United States Patent
Sakamoto et al.

(10) Patent No.: US 7,876,910 B2
(45) Date of Patent: Jan. 25, 2011

(54) VEHICULAR ACTIVE NOISE/VIBRATION/SOUND CONTROL SYSTEM, AND VEHICLE INCORPORATING SUCH SYSTEM

(75) Inventors: Kosuke Sakamoto, Utsunomiya (JP); Toshio Inoue, Tochigi-ken (JP); Akira Takahashi, Tochigi-ken (JP); Yasunori Kobayashi, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 1275 days.

(21) Appl. No.: 11/442,357

(22) Filed: May 30, 2006

(65) Prior Publication Data

US 2006/0269078 A1 Nov. 30, 2006

(30) Foreign Application Priority Data

May 30, 2005 (JP) ............................ 2005-157662

(51) Int. Cl.
*A61F 11/06* (2006.01)
*G10K 11/16* (2006.01)
*H03B 29/00* (2006.01)

(52) U.S. Cl. ....................................... 381/71.4; 381/86

(58) Field of Classification Search ....... 381/71.2–71.4, 381/86, 94.1, 73.1
See application file for complete search history.

(56) References Cited

U.S. PATENT DOCUMENTS

| | | | | |
|---|---|---|---|---|
| 4,506,380 | A * | 3/1985 | Matsui | 381/71.9 |
| 5,245,664 | A * | 9/1993 | Kinoshite et al. | 381/71.4 |
| 5,485,523 | A * | 1/1996 | Tamamura et al. | 381/71.4 |
| 5,635,903 | A * | 6/1997 | Koike et al. | 340/441 |
| 5,748,748 | A * | 5/1998 | Fischer et al. | 381/71.4 |
| 6,592,375 | B2 * | 7/2003 | Henry et al. | 434/62 |
| 7,357,220 | B2 * | 4/2008 | Horikou | 181/250 |

FOREIGN PATENT DOCUMENTS

| | | | |
|---|---|---|---|
| JP | 09-060515 | A | 3/1997 |
| JP | 3261128 | B2 | 12/2001 |
| JP | 2004-074995 | A | 3/2004 |
| WO | 90/13109 | A1 | 11/1990 |

* cited by examiner

*Primary Examiner*—Vivian Chin
*Assistant Examiner*—Jason R Kurr
(74) *Attorney, Agent, or Firm*—Arent Fox, LLP

(57) ABSTRACT

An active noise/vibration/sound control system for a vehicle has an ANC (active noise control apparatus), an AVC (active vibration control apparatus), and an ASC (active sound control apparatus). To prevent the ANC, the AVC, and the ASC from interfering with each other and hence to prevent vehicle cabin environment of vibrations, noise, and sound from being impaired, activation and inactivation of the ANC, the AVC, and the ASC are controlled or their control characteristics are controlled in relation to each other by a weighting variable calculator as a coordination controller, depending on an engine rotation frequency and a frequency change which are representative of a running state of the vehicle as detected by an engine rotation frequency detector and a frequency change detector that serve as a running state detector.

10 Claims, 10 Drawing Sheets

MP1 (AVC)

| Δaf \ fe[Hz] | 60 | 80 | 90 | 100 | 110 |
|---|---|---|---|---|---|
| 10 | 1 | 1 | 1 | 0. 6 | 0 |
| 20 | 0. 8 | 0. 7 | 0. 4 | 0. 2 | 0 |
| 30 | 0. 3 | 0. 2 | 0. 1 | 0. 1 | 0 |
| 40 | 0 | 0 | 0 | 0 | 0 |
| 50 | 0 | 0 | 0 | 0 | 0 |

MP2 (ANC)

| Δaf \ fe[Hz] | 60 | 80 | 90 | 100 | 110 |
|---|---|---|---|---|---|
| 10 | 1 | 1 | 0 | 0 | 0 |
| 20 | 0. 6 | 0. 7 | 0 | 0 | 0 |
| 30 | 0. 3 | 0. 2 | 0 | 0 | 0 |
| 40 | 0. 2 | 0 | 0 | 0 | 0 |
| 50 | 0. 1 | 0 | 0 | 0 | 0 |

MP3 (ASC)

| Δaf \ fe[Hz] | 60 | 80 | 90 | 100 | 110 |
|---|---|---|---|---|---|
| 10 | 0 | 0 | 0. 1 | 0. 3 | 0. 2 |
| 20 | 0. 4 | 0. 3 | 0. 4 | 0. 6 | 0. 3 |
| 30 | 0. 7 | 0. 8 | 0. 9 | 0. 8 | 0. 4 |
| 40 | 0. 8 | 0. 8 | 1 | 1 | 0. 4 |
| 50 | 0. 9 | 0. 7 | 1 | 1 | 0. 5 |

MP3a

| Δaf \ fe[Hz] | 60 | 80 | 90 | 100 | 110 |
|---|---|---|---|---|---|
| 10 | 0 | 0 | 0 | 0 | 0 |
| 20 | 0 | 0 | 0 | 0 | 0 |
| 30 | 0. 1 | 0. 2 | 0. 1 | 0 | 0 |
| 40 | 0. 2 | 0. 2 | 0. 2 | 0. 1 | 0 |
| 50 | 0. 3 | 0. 3 | 0. 3 | 0 | 0 |

MP3m

| Δaf \ fe[Hz] | 60 | 80 | 90 | 100 | 110 |
|---|---|---|---|---|---|
| 10 | 0 | 0. 2 | 0. 1 | 0 | 0 |
| 20 | 0. 2 | 0. 4 | 0. 2 | 0. 2 | 0. 1 |
| 30 | 0. 2 | 0. 4 | 0. 6 | 0. 5 | 0. 1 |
| 40 | 0. 3 | 0. 6 | 0. 8 | 0. 7 | 0. 2 |
| 50 | 0. 4 | 0. 7 | 1 | 1 | 0. 3 |

VEHICULAR ACTIVE NOISE/VIBRATION/SOUND CONTROL SYSTEM, AND VEHICLE INCORPORATING SUCH SYSTEM

BACKGROUND OF THE INVENTION

1. Field of the Invention

The present invention relates to a vehicular active noise/vibration/sound control system having at least two of an active noise control apparatus (hereinafter referred to as "ANC") for reducing noise in a vehicle cabin based on a detected signal representative of engine vibrations, an active vibration control apparatus (hereinafter referred to as "AVC") for reducing vehicle vibrations based on the above detected signal, and an active sound control apparatus (hereinafter referred to as "ASC") for generating a sound effect in the vehicle cabin based on the above detected signal, and a vehicle incorporating such a vehicular active noise/vibration/sound control system.

2. Description of the Related Art

FIG. 8 of the accompanying drawings schematically shows an ANC-mounted vehicle 10N developed by the applicant of the present application. As shown in FIG. 8, the ANC-mounted vehicle 10N has an engine 12 whose ignition control is performed by an engine ECU 14 and which supplies engine rotation pulses Ep corresponding to explosion periods of the engine 12 through the engine ECU 14 to an ANC 16.

Noise that is primarily generated by explosions in the engine 12 is perceived by the ears of passengers seated on front and rear seats of the ANC-mounted vehicle 10N. Microphones 18, 20 are fixedly positioned on the interior roof or upper portion of seats near the ears of the passengers. Speakers 22, 24 fixedly mounted in the ANC-mounted vehicle 10N near the front and rear seats radiate canceling sounds for minimizing the sounds (noise) that are applied to the microphones 18, 20. The ANC 16 generates control signals S1, S2 that are supplied to the speakers 22, 24 to radiate the canceling sounds.

The ANC 16 comprises a reference signal generator 26 for generating a sine-wave reference signal proportional to the frequency of engine rotation cycles from the engine rotation pulses Ep and a pair of adaptive filters 28, 30 for changing the phase and amplitude of the reference signal to generate the control signals S1, S2 to minimize output signals from the microphones 18, 20.

FIG. 9 of the accompanying drawings schematically shows an AVC-mounted vehicle 10V developed by the applicant of the present application. Those parts of the AVC-mounted vehicle 10V which are identical to the ANC-mounted vehicle 10N shown in FIG. 8 are denoted by identical reference characters, and will not be described in detail below.

As shown in FIG. 9, the engine 12 is installed on a vehicle chassis by engine mounts 42, 44. The engine mounts 42, 44 incorporate respective actuators which are vibratable in synchronism with vibrations of the engine 12 to prevent the vibrations of the engine 12 from being transmitted to the vehicle chassis. The engine mounts 42, 44 are combined with respective load sensors 46, 48 doubling as vibration sensors. An AVC 50 generates control signals S3, S4 and supplies the control signals S3, S4 to the actuators of the engine mounts 42, 44 to cause the actuators to vibrate for thereby isolating the vibrations of the engine 12.

The load sensors 46, 48 supply their output signals to the AVC 50. The engine rotation pulses Ep are also supplied to the AVC 50.

The AVC 50 comprises the reference signal generator 26 for generating a sine-wave reference signal proportional to the frequency of engine rotation cycles from the engine rotation pulses Ep and a pair of adaptive filters 52, 54 for changing the phase and amplitude of the reference signal to generate the control signals S3, S4 to minimize changes in output signals from the load sensors 46, 48.

FIG. 10 of the accompanying drawings schematically shows an ASC-mounted vehicle 10S developed by the applicant of the present application. Those parts of the ASC-mounted vehicle 10S which are identical to the ANC-mounted vehicle 10N and AVC-mounted vehicle 10V shown in FIGS. 8 and 9 are denoted by identical reference characters, and will not be described in detail below.

The ASC-mounted vehicle 10S has an ASC 60 comprising the reference signal generator 26 for generating a sine-wave reference signal proportional to the frequency of engine rotation cycles from the engine rotation pulses Ep and a pair of acoustic controllers 56, 58 for changing the phase and amplitude of the reference signal to generate control signals S5, S6. The control signals S5, S6 are supplied to the speakers 22, 24 to cause the speakers 22, 24 to radiate a sound effect depending on the acceleration of the ASC-mounted vehicle 10S.

It may be proposed to install all the ANC 16, the AVC 50, and the ASC 60 in a vehicle to provide a more comfortable vehicle cabin environment.

There has been proposed a vehicular acoustic enhancement system including an ASC having a sound source for generating a sound effect and an ANC having an adaptive noise cancellation controller (see Japanese Patent No. 3261128). In the disclosed vehicular acoustic enhancement system, while the vehicle is being accelerated, the sound source outputs an accelerating sound simulating that of a high-output vehicle through a mixer and speakers, and the adaptive noise cancellation controller generates a noise cancellation signal based on a signal obtained from the engine and representing an engine rotational speed and a reference signal obtained from a microphone and supplies the noise cancellation signal to the mixer.

However, the vehicular acoustic enhancement system disclosed in Japanese Patent No. 3261128 is disadvantageous in that since the ASC and the ANC are activated at all times, they may interfere with each other depending on the running state of the vehicle, possibly impairing the noise and acoustic environment in the vehicle.

For example, when the ASC operates to emphasize the accelerating sound upon acceleration of the vehicle, the ANC operates to cancel the accelerating sound. As a result, the driver of the vehicle is unable to enjoy acceleration as is otherwise felt by the emphasized accelerating sound.

SUMMARY OF THE INVENTION

It is therefore an object of the present invention to provide a vehicular active noise/vibration/sound control system which has at least two of an ANC, an AVC, and an ASC and which is arranged to prevent the ANC, the AVC, and the ASC from interfering with each other to impair a vibratory acoustic (noise) environment, and a vehicle incorporating such a vehicular active noise/vibration/sound control system.

According to the present invention, there is provided an active noise/vibration/sound control system for use in a vehicle, having at least two of an active noise control apparatus for reducing noise in a vehicle cabin based on a detected signal representative of engine vibrations, an active vibration control apparatus for reducing vehicle vibrations based on the detected signal, and an active sound control apparatus for generating a sound effect in the vehicle cabin based on the detected signal, the active noise/vibration/sound control system comprising running state detecting means for detecting a running state of the vehicle, and coordination control means for controlling activation and inactivation of the active noise control apparatus, the active vibration control apparatus, and the active sound control apparatus or controlling control characteristics thereof in relation to each other, depending on the detected running state.

With the above arrangement, depending on the running state of the vehicle detected by the running state detecting means, activation and inactivation of the active noise control apparatus, the active vibration control apparatus, and the active sound control apparatus are controlled or control characteristics thereof are controlled in relation to each other. Therefore, in the active noise/vibration/sound control system having at least two of the active noise control apparatus, the active vibration control apparatus, and the active sound control apparatus, these apparatus are prevented from interfering with each other and hence a vibratory acoustic (noise) environment in the vehicle is prevented from being impaired.

The running state detecting means may have an engine rotation frequency detector for detecting an engine rotation frequency and a frequency change detector for detecting a frequency change in the detected engine rotation frequency, and the coordination control means may comprise a weighting variable calculator for calculating weighting variables for control signals to be applied respectively to the active noise control apparatus, the active vibration control apparatus, and the active sound control apparatus, based on the engine rotation frequency and the frequency change. The active noise/vibration/sound control system thus constructed is relatively simple in arrangement.

If the vehicle has a transmission selectively operable in an automatic transmission mode and a manual transmission mode, then the weighting variable calculator may change weighting variables for the control signal to be applied to the active sound control apparatus depending on whether the transmission operates in the automatic transmission mode or the manual transmission mode. With this arrangement, the control apparatus may be controlled in a manner matching the selected transmission mode, e.g., to generate a sound effect in the vehicle to give the passengers in the vehicle sporty feeling when the transmission is in the manual transmission mode.

According to the present invention, since activation and inactivation of the active noise control apparatus, the active vibration control apparatus, and the active sound control apparatus are controlled or control characteristics thereof are controlled in relation to each other by the coordination control means depending on the running state of the vehicle detected by the running state detecting means, the control apparatus of the active noise/vibration/sound control system having at least two of the active noise control apparatus, the active vibration control apparatus, and the active sound control apparatus are prevented from interfering with each other and hence the vibratory acoustic (noise) environment in the vehicle is prevented from being impaired.

If the transmission of the vehicle is selectively operable in the automatic transmission mode and the manual transmission mode, then the weighting variable calculator changes weighting variables for the control signal to be applied to the active sound control apparatus depending on whether the transmission operates in the automatic transmission mode or the manual transmission mode. Therefore, a sound effect matching the selected transmission mode can be generated.

The present invention is also applied to a vehicle incorporating an active noise/vibration/sound control system having at least two of an active noise control apparatus for reducing noise in a vehicle cabin based on a detected signal representative of engine vibrations, an active vibration control apparatus for reducing vehicle vibrations based on the detected signal, and an active sound control apparatus for generating a sound effect in the vehicle cabin based on the detected signal.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 8:
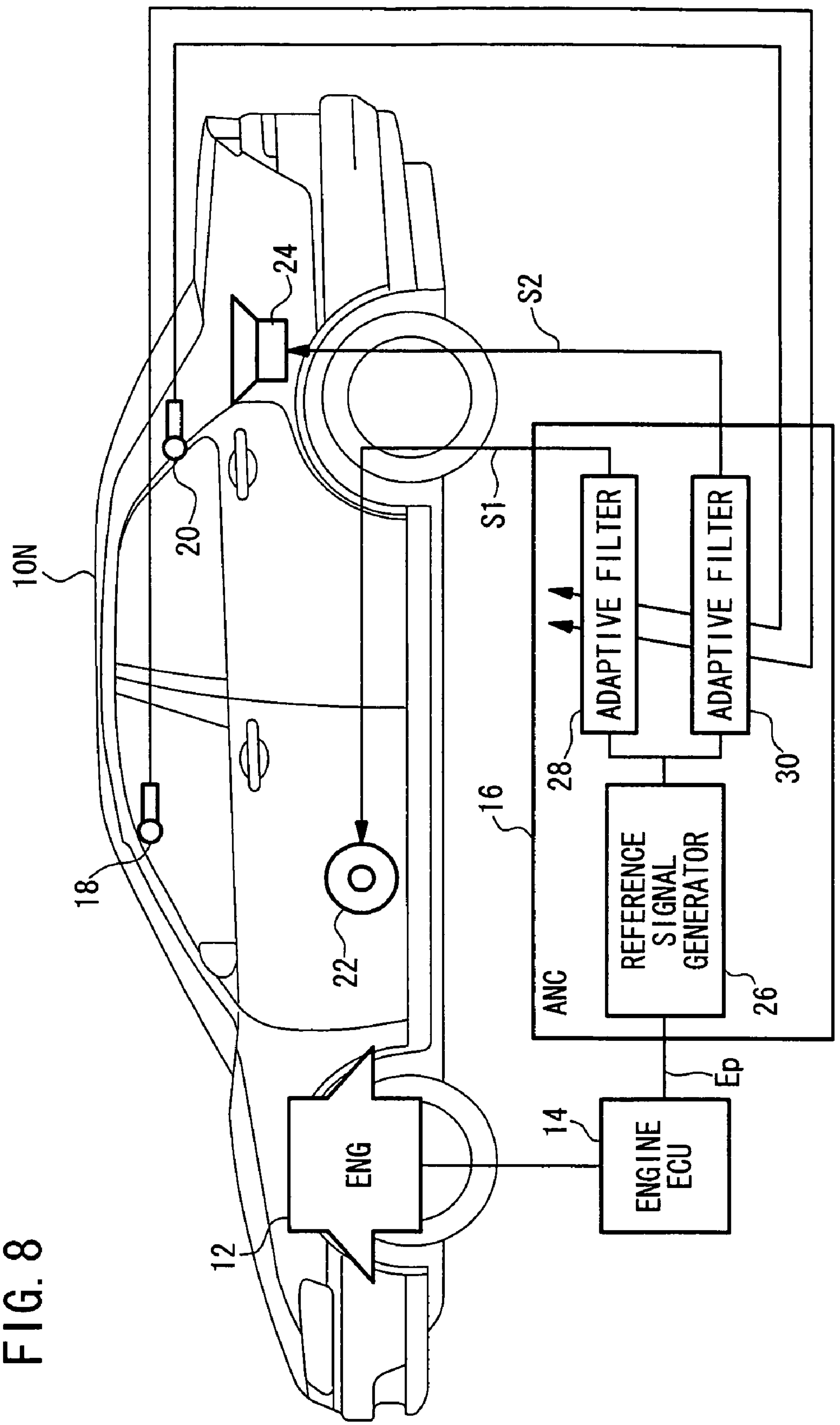
FIG. 8 is a schematic side elevational view of an ANC-mounted vehicle developed by the applicant of the present application.
Figure 9:
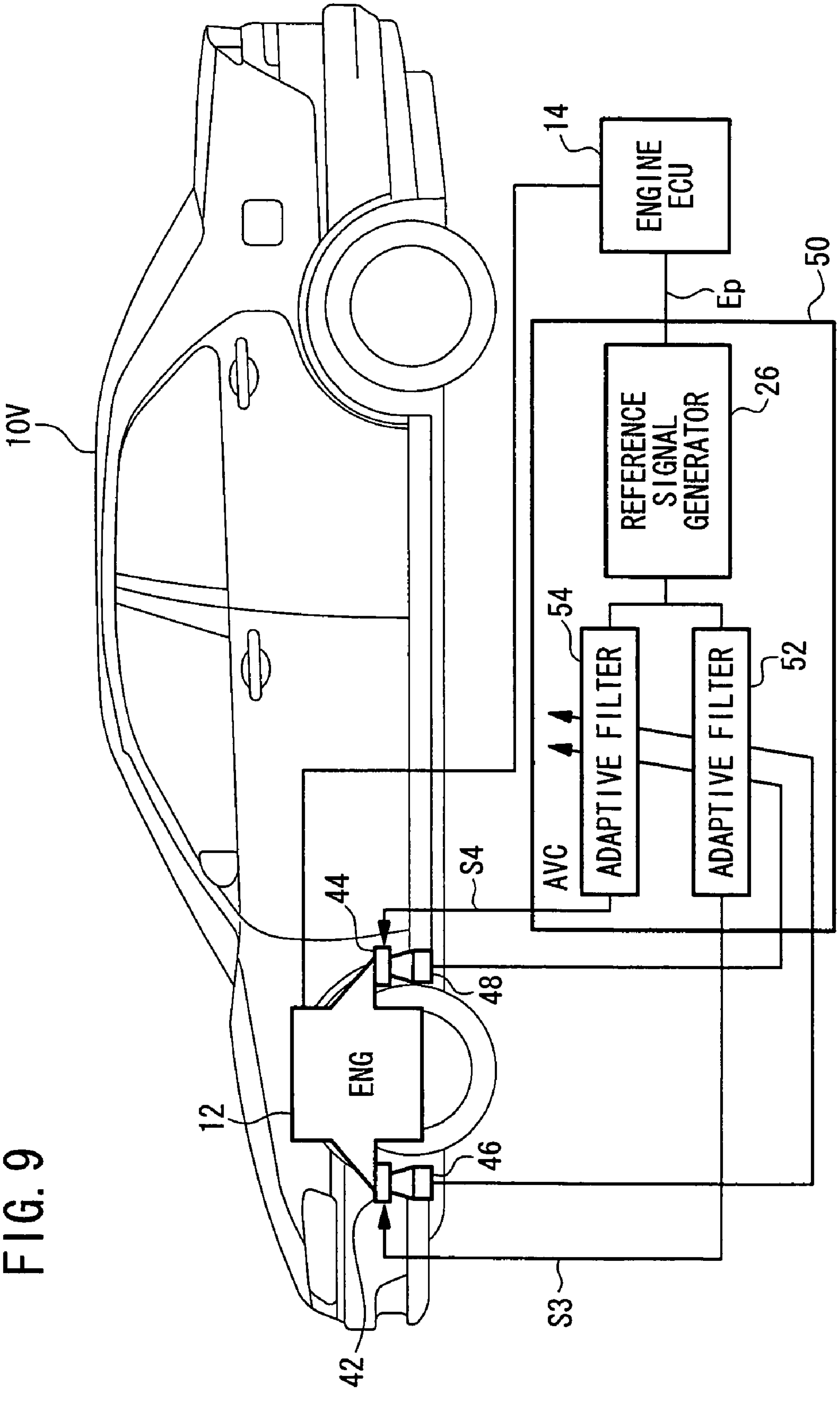
FIG. 9 is a schematic side elevational view of an AVC-mounted vehicle developed by the applicant of the present application.
Figure 10:
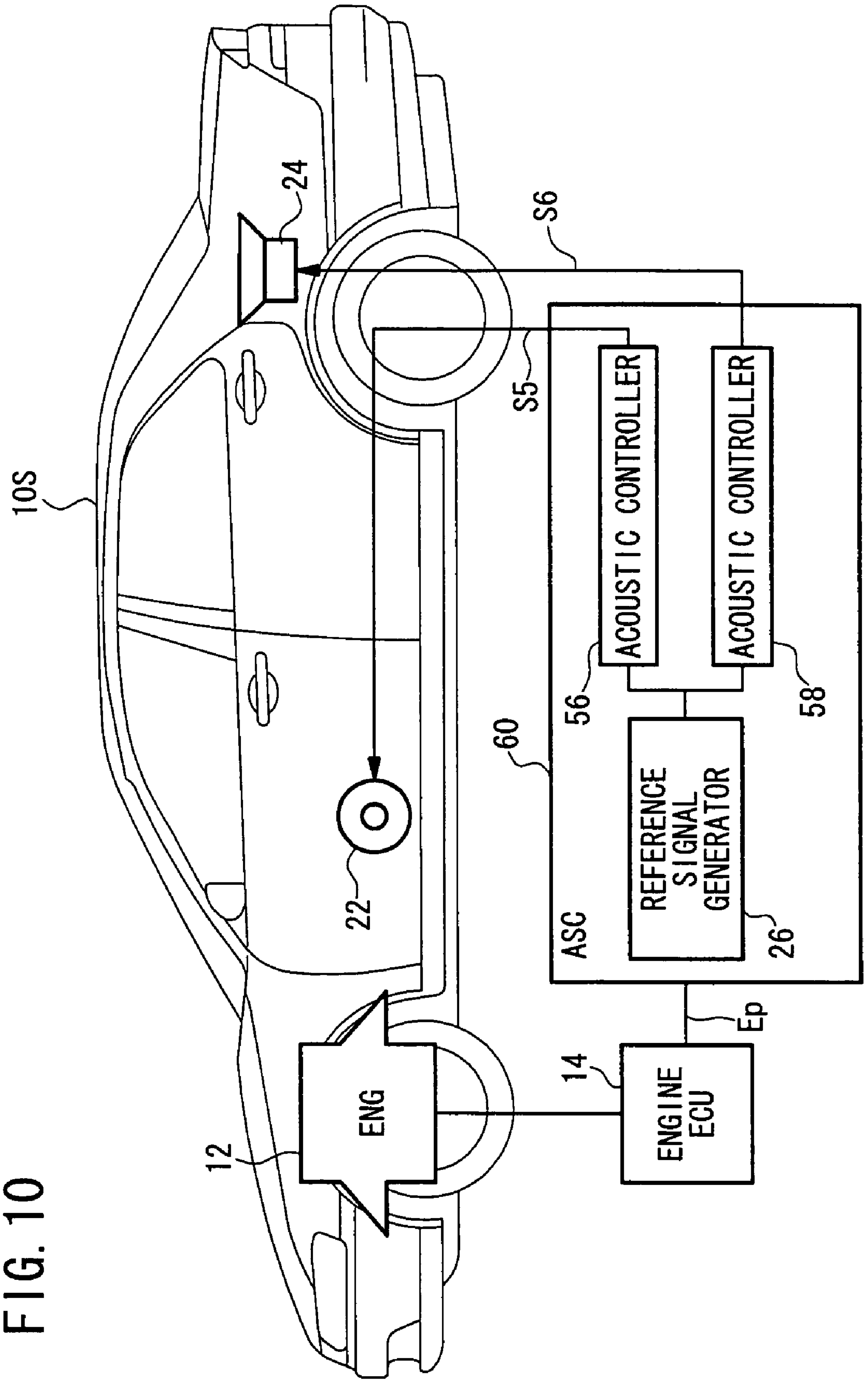
FIG. 10 is a schematic side elevational view of an ASC-mounted vehicle developed by the applicant of the present application.

Preferred embodiments of the present invention will be described below with reference to the drawings. Those parts of the preferred embodiments which are identical to those shown in FIGS. 8 through 10 are denoted by identical reference characters.

Figure 1:
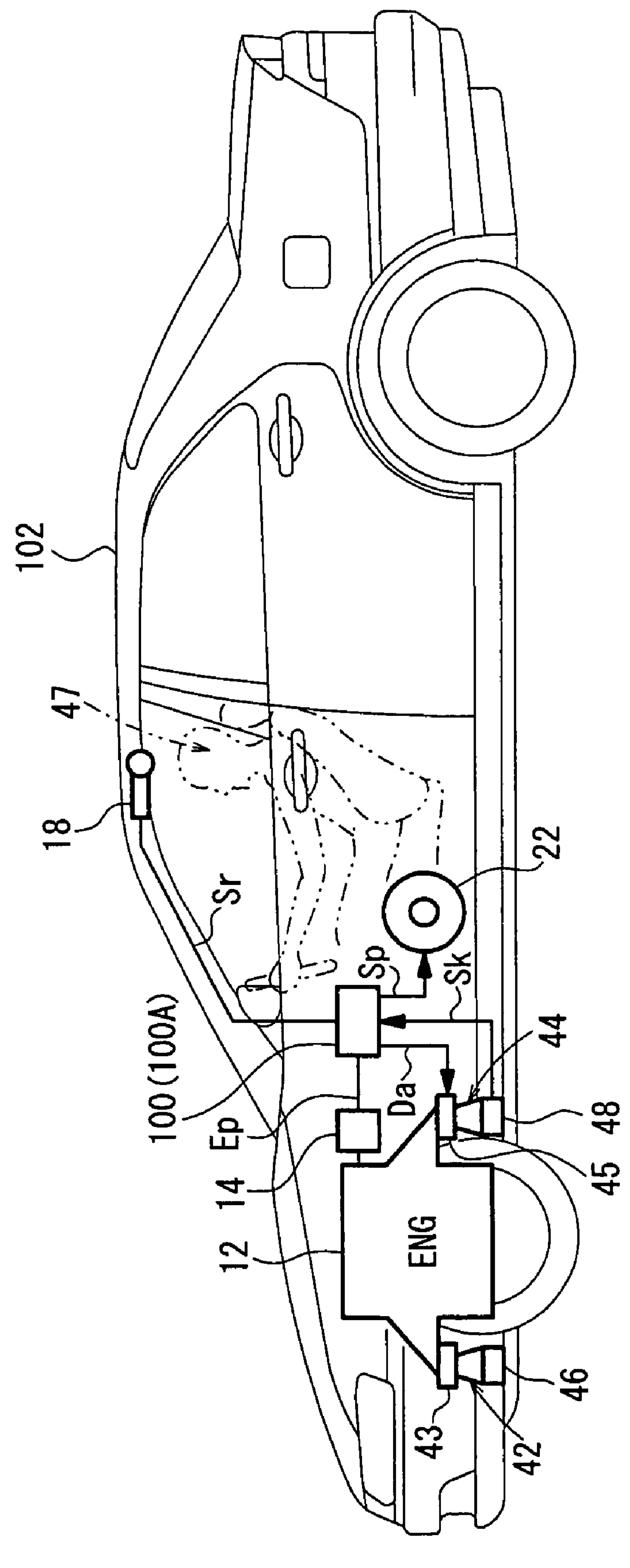
FIG. 1 is a schematic side elevational view of a vehicle incorporating a vehicular active noise/vibration/sound control system (hereinafter referred to as "noise/vibration/sound control ECU") according to a first embodiment of the present invention.

FIG. 1 schematically shows a vehicle 102 incorporating a vehicular active noise/vibration/sound control system (hereinafter referred to as "noise/vibration/sound control ECU") 100 according to a first embodiment of the present invention. The vehicle 102 may alternatively incorporate a noise/vibration/sound control ECU 100A, to be described later, according to a second embodiment of the present invention.

As shown in FIG. 1, the vehicle 102 has an engine 12 which is mounted on a vehicle chassis (not shown) and whose ignition control is performed by an engine ECU 14.

A detector, not shown, detects the frequency of rotation cycles of the main shaft of the engine 12, and produces engine rotational pulses Ep corresponding to explosion periods of the engine 12. The engine rotational pulses Ep are supplied through the engine ECU 14 to the noise/vibration/sound control ECU 100.

The engine 12 is installed on the vehicle chassis by engine mounts 42, 44. The engine mounts 42, 44 have respective load sensors 46, 48 doubling as vibration sensors and respective actuators (vibration actuators) 43, 45 which apply vibrations to the engine 12 through the respective engine mounts 42, 44.

A microphone 18 is fixed to the interior roof of the vehicle 102 at a transversely central position close to a passenger position 47, i.e., the position of an ear of the driver in the present embodiment. Speakers 22 for radiating acoustic sounds to passengers are fixedly mounted respectively on the inner panels of respective front doors on both sides.

Actually, other speakers are installed near rear seats and microphones are installed near rear-seat passenger positions, as shown in FIG. 8. In the present embodiment, however, these speakers and microphones are omitted from illustration for an easier understanding of the present invention. In addition, the engine mounts 42, 44 are actually separately controlled as shown in FIG. 9. In the present embodiment, however, only the control of the engine mount 44 will be described below for an easier understanding of the present invention.

The noise/vibration/sound control ECU 100 is supplied with the engine rotation pulses Ep, a reference signal Sr from the microphone 18, and a load signal Sk from the load sensor 48, and outputs a control signal Da as a drive signal for the actuator 45 and a control signal Sp as a drive signal for the speaker 22, respectively to the actuator 45 and the speaker 22.

Figure 2:
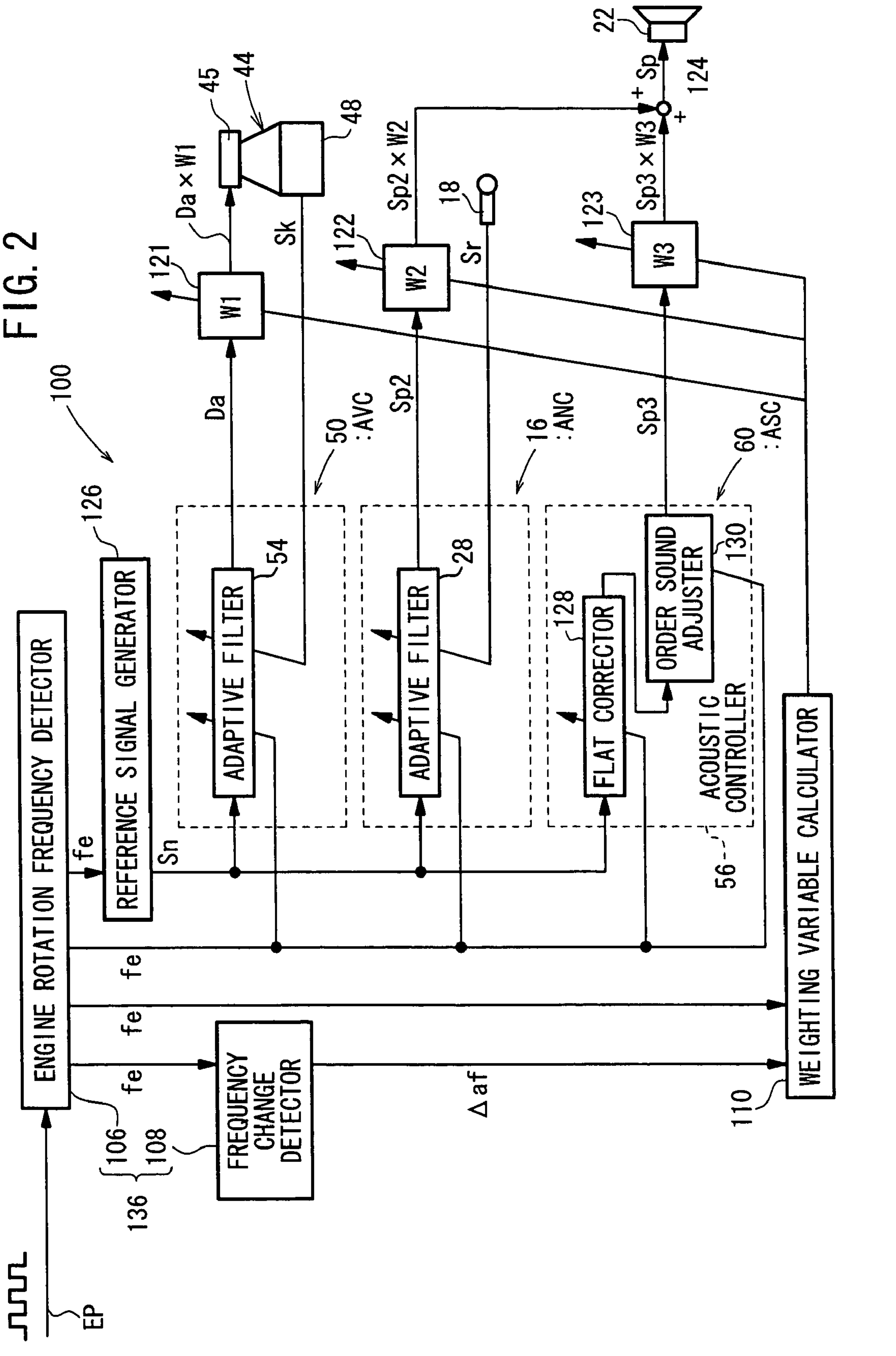
FIG. 2 is a block diagram of the noise/vibration/sound control ECU shown in FIG. 1.

FIG. 2 shows in block form the noise/vibration/sound control ECU 100 according to the first embodiment.

As shown in FIG. 2, the noise/vibration/sound control ECU 100 comprises an active vibration control apparatus (hereinafter referred to as "AVC") 50 for reducing vibrations of the vehicle 102, the AVC 50 having an adaptive filter 54 and a reference signal generator 126, an active noise control apparatus (hereinafter referred to as "ANC") 16 for reducing noise in the vehicle cabin of the vehicle 102, the ANC 16 having an adaptive filter 28 and the reference signal generator 126, and an active sound control apparatus (hereinafter referred to as "ASC") 60 for generating a sound effect in the vehicle cabin of the vehicle 102, the ASC 60 having an acoustic controller 56 and the reference signal generator 126, The frequency of the engine rotation pulses Ep (hereinafter referred to as "engine rotation frequency fe") is supplied from an engine rotation frequency detector 106 to the AVC 50, the ANC 16, the ASC 60, etc. The engine rotation frequency detector 106 comprises a frequency counter or the like for detecting, i.e., calculating, the engine rotation frequency fe from the engine rotation pulses Ep, which are generated by a Hall device or the like when the output shaft of the engine 12 makes revolutions.

Figure 3:
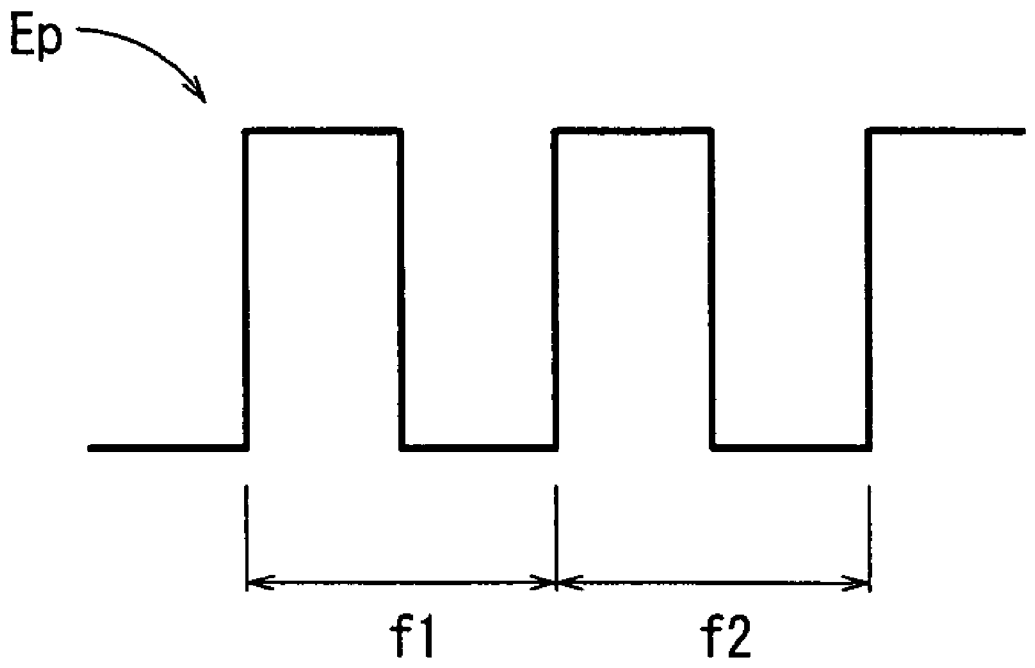
FIG. 3 is a diagram showing the waveform of engine pulses.

FIG. 3 shows the waveform of the engine rotation pulses Ep. A frequency change detector 108 detects a frequency change Δaf from the engine rotation pulses Ep. Specifically, the frequency change detector 108 determines the difference Δf (Δf=f2−f1) between the engine rotation frequency fe=f1 (preceding frequency) of a preceding pulse and the engine rotation frequency fe=f2 (present frequency) of a present pulse, the preceding and present pulses being successively detected by the engine rotation frequency detector 106, and multiplies the difference Δf by the present engine rotation frequency fe=f2, thereby determining the frequency change Δaf per unit time of the engine rotation frequency fe (Δaf=Δf×f2) [(cycle·cycle/(second·second)], i.e., an acceleration.

It is known that the frequency change Δaf is of a different value depending on which gear position the transmission of the vehicle 102 is in. Specifically, the frequency change Δaf is greater when the transmission is in a lower gear position and is smaller when the transmission is in a higher gear position.

The engine rotation frequency detector 106 and the frequency change detector 108 jointly make up a running state detecting means 136 according to the present embodiment.

The reference signal generator 126 generates a sine-wave reference signal Sn of harmonics (integral multiples and/(or) real number multiples ranging from the first to sixth harmonics) which matches the type of the vehicle 102 based on the engine rotation frequency fe.

Harmonics to be generated with respect to the adaptive filter 54 of the AVC 50 and the adaptive filter 28 of the ANC 16 are determined as follows: Gain characteristics (transfer characteristics defined by frequencies [Hz] on a horizontal axis and gains [dB] on a vertical axis) according to various vibration characteristics and noise characteristics of an entire system of the AVC 50 and the ANC 16 depending on the vehicle type to be applied are measured in advance. Then, the reference signal generator 126 generates a sine-wave reference signal Sn of one or more harmonics corresponding to the measured frequency range.

The acoustic controller 56 of ASC 60 is supplied with three reference signals Sn of orders corresponding to harmonics that are four, five, and six times, for example, the engine rotation frequency fe in order to produce a sporty sound effect (alternatively, a brisk sound effect or a massive sound effect) in view of human sensitivity.

A weighting variable calculator 110, which functions as a coordination control means, calculates weighting variables W1, W2, W3 to be set respectively in weighting units 121, 122, 123 that are connected between the output terminals of the AVC 50, ANC 16, and the ASC 60, and the actuator 45 of the engine mount 44 to be controlled and the speaker 22, based on the engine rotation frequency fe and the frequency change Δaf. Each of the weighting variables W1, W2, W3 has a value in the range from 0 to 1.

The weighting unit 121 weights a control signal Da output from the adaptive filter 54, and outputs a control signal Da×W1 to the actuator 45 to be controlled.

The weighting unit 122 weights a control signal Sp2 output from the adaptive filter 28, and outputs a control signal Sp2×W2 as the control signal Sp for the speaker 22 to be controlled.

The weighting unit 123 weights a control signal Sp3 output from the acoustic controller 56, and outputs a control signal Sp3×W3 as the control signal Sp for the speaker 22 to be controlled.

The control signal Sp for the speaker 22 is a combined signal (added signal) produced when the control signal Sp2×W2 and the control signal Sp3×W3 are combined with (added to) each other by an adder 124.

The adaptive filter 54 of the AVC 50 adaptively changes the amplitude and phase of the reference signal Sn to generate a control signal Da for reducing a change in the load signal Sk, based on the engine rotation frequency fe and the load signal (detected signal) Sk which has been detected by the load sensor 48 and converted into an electric signal, and outputs the generated control signal Da.

The adaptive filter 28 of the ANC 16 adaptively changes the amplitude and phase of the reference signal Sn to generate a control signal Sp2 for reducing the amplitude of the reference signal Sr which has been picked up by the microphone 18 and converted into an electric signal, based on the engine rotation frequency fe and the reference signal Sr from the microphone 18, and outputs the generated control signal Sp2.

Each of the engine rotation frequency detector 106, the frequency change detector 108, the load sensor 48, and the microphone 18 functions as a transducer.

The acoustic controller 56 of the ASC 60 comprises a flat corrector 128 and an order sound adjuster 130. The flat corrector 128 comprises three filters corresponding to the above orders, i.e., 4, 5, and 6, and having inverse gain characteristics which are an inversion of measured gain characteristics (defined by frequencies [Hz] on a horizontal axis and gains [dB] on a vertical axis, and referred to as "cabin sound field transfer characteristics") from the reference signal generator 126 to the acoustic controller 56, the weighting unit 123, the adder 124, and the speaker 22 and from the speaker 22 to the passenger position 47 (the position of the microphone 18 in the present embodiment). In the flat corrector 128, these three filters adaptively change the amplitude and phase of the reference signals Sn of the orders 4, 5, 6 to generate respective control signals corresponding to the orders 4, 5, 6 for providing flat gain characteristics at the position of the microphone 18.

The order sound adjuster 130 of the ASC 60 comprises three adaptive filters corresponding to the respective corrected reference signals Sn of the orders 4, 5, 6 which are output from the flat corrector 128. The order sound adjuster 130 adaptively changes the amplitude and phase of the corrected reference signals Sn of the orders 4, 5, 6 and combines the reference signals Sn into a control signal Sp3 for controlling the speaker 22 to produce a sound effect depending on the engine rotation frequency fe.

Figure 4:
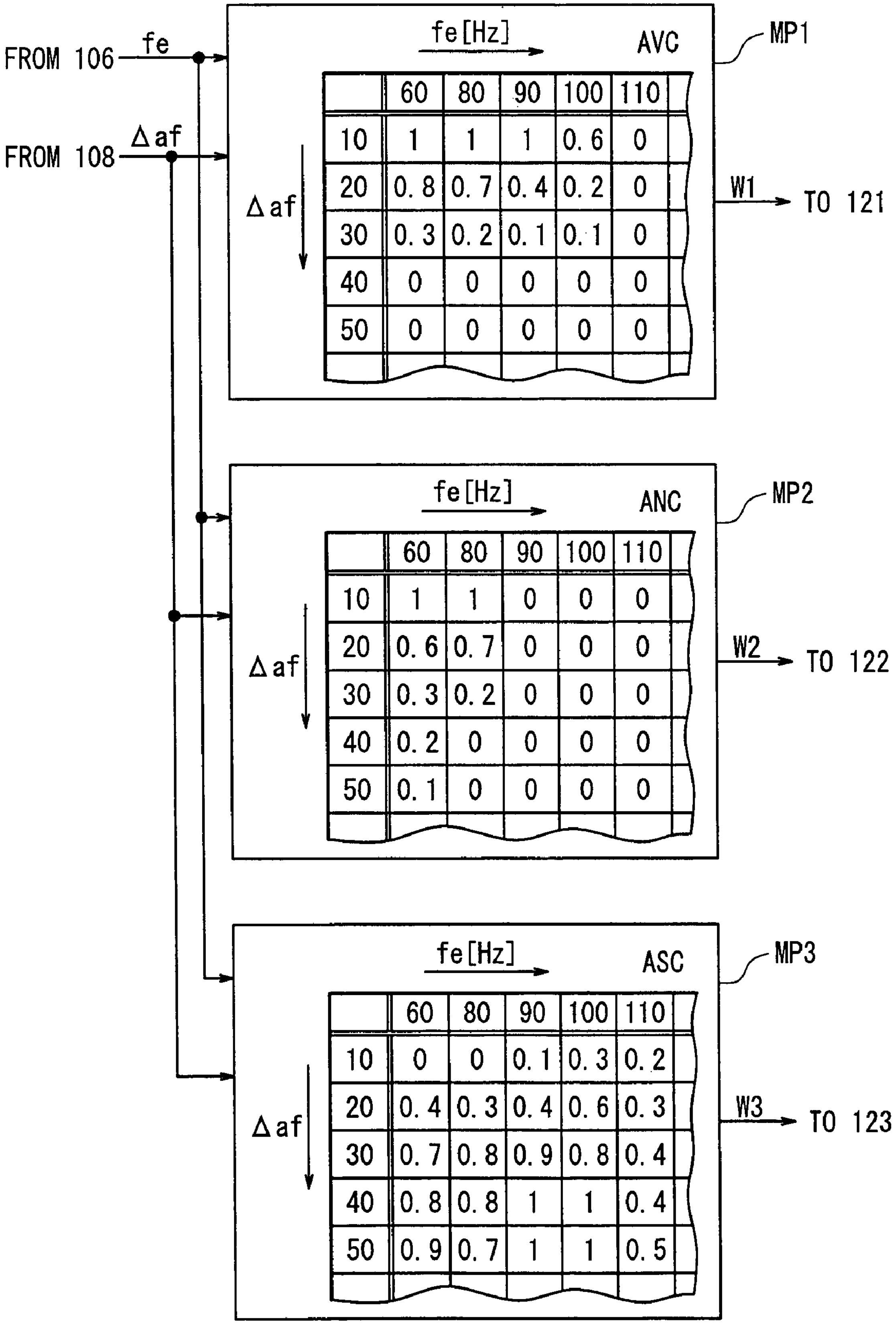
FIG. 4 is a diagram of weighting variable maps which are stored in a memory of a weighting variable calculator.

FIG. 4 shows by way of example three maps MP1, MP2, MP3 of weighting variables W, i.e., weighting variables W1 for the AVC 50, weighting variables W2 for the ANC 16, and weighting variables W3 for the ASC 60, which are stored in a memory of the weighting variable calculator 110. The weighting variables W are set to optimum values depending on the type of the vehicle 102.

A weighting variable W1 for the AVC 50, a weighting variable W2 for the ANC 16, and a weighting variable W3 for the ASC 60 shown in FIG. 4 are calculated, i.e., read from the memory, using the engine rotation frequency fe and the frequency change Δaf as an address. The calculated weighting variables W1, W2, W3 are then set respectively in the weighting units 121, 122, 123.

Figure 5:
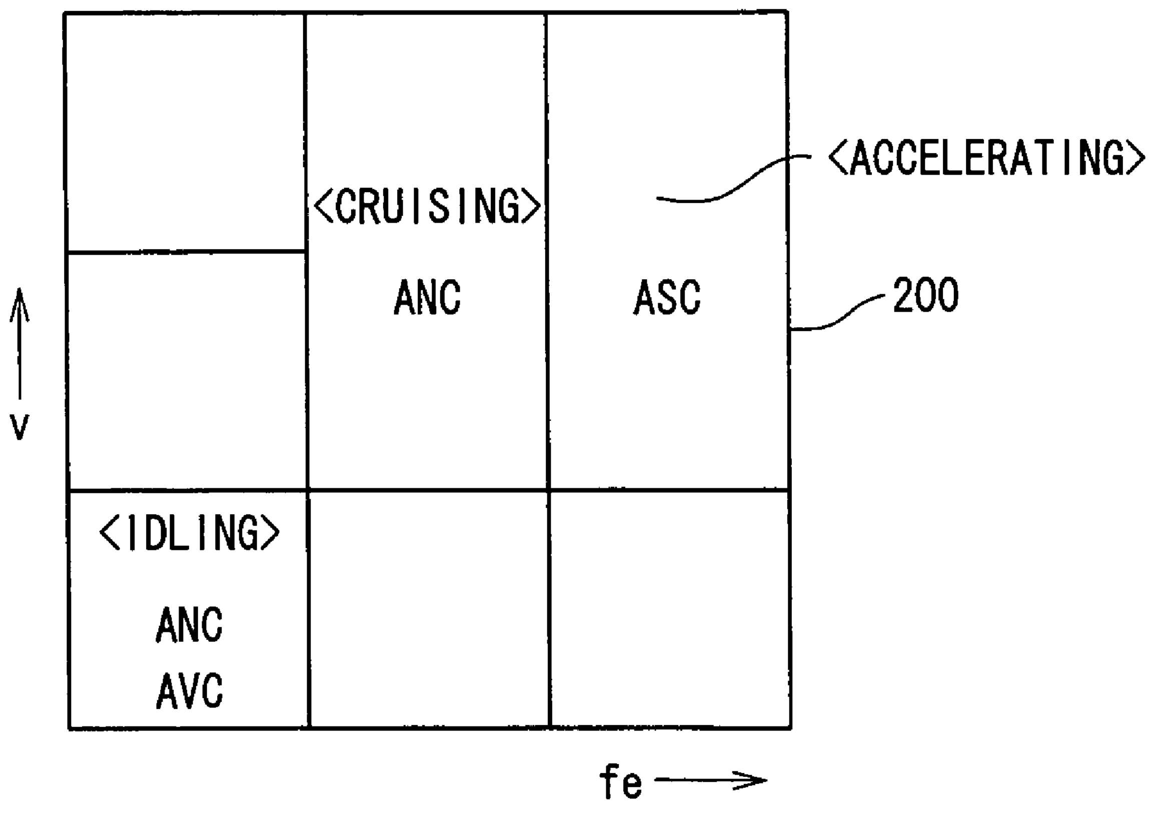
FIG. 5 is a diagram showing a control apparatus inactivating and activating table as an index for determining weighting variables.

FIG. 5 shows a control apparatus inactivating and activating table 200 of the control apparatus (the AVC 50, the ANC 16, the ASC 60) to be operated depending on running states (defined by the engine rotation frequency fe on a horizontal axis and the vehicle speed v on a vertical axis) of the vehicle 102, the control apparatus inactivating and activating table 200 serving as an index indicative of a basic concept for determining weighting variables W1, W2, W3 in the weighting variable maps MP1, MP2, MP3 shown in FIG. 4.

According to the control apparatus inactivating and activating table 200 shown in FIG. 5, in a range (referred to as an idling range) in which the engine rotation frequency fe is low and the vehicle speed v is low, the ASC 60 is inactivated and no sound effect is generated, and the ANC 16 and the AVC 50 are operated to keep quiet in the vehicle cabin and reduce vibrations.

In a range (referred to as an accelerating range) in which the engine rotation frequency fe is high and the vehicle speed v is in a medium speed range and a high speed range for acceleration, only the ASC 60 is operated to generate a sound effect to give the driver and other passengers a sporty feeling, and the AVC 50 and the ANC 16 are inactivated to allow the driver and other passengers to realistically feel vibrations and noise generated on the vehicle 102 to enjoy active driving.

In a range (referred to as a cruising range) in which the engine rotation frequency fe is medium and the vehicle speed v is in the medium speed range and the high speed range for cruising, only the ANC 16 is operated to reduce noise, the AVC 50 is inactivated because vibrations are relatively small, and the ASC 60 is also inactivated as no sound effect for acceleration is required.

Since the ANC 16, the AVC 50 and the ASC 60 are controlled in a coordinated way as indicated by the control apparatus inactivating and activating table 200, vehicle cabin environment of vibrations, noise and sound is prevented from being impaired because the ANC 16, the AVC 50, and the ASC 60 are not independently controlled and are prevented from interfering with each other.

The map MP1 for the AVC 50 which has been tested many times on particular vehicle types and the vehicle 102 based on the index shown in FIG. 5 and simulated and actually generated is arranged such that when the engine rotation frequency fe is low and the frequency change Δaf is low, the weighting variable W1 is set to 1 (Da=Da×W1) for effectively activating the AVC 50, and as the engine rotation frequency fe is higher and the frequency change Δaf is higher, the weighting variable W1 gradually changes from 1 to 0.

The map MP2 for the ANC 16 is arranged such that when the engine rotation frequency fe is low and medium and the frequency change Δaf is low and medium, the weighting variable W2 is set to 1 (Da=Da×W2) for effectively activating the ANC 16, and as the engine rotation frequency fe is higher and the frequency change Δaf is higher, the weighting variable W2 gradually changes from 1 to 0. When the engine rotation frequency fe is in a range higher than 90 [Hz], then the weighting variable W2 is set to 0 to inactivate the ANC 16. Therefore, the ANC 16 is inactivated in the accelerating range.

The map MP3 for the ASC 60 is arranged such that when the engine rotation frequency fe is low and the frequency change Δaf is low, the weighting variable W3 is set to 0 (Da=Da×W3) for inactivating the ASC 60, and as the engine rotation frequency fe and the frequency change Δaf are higher, the weighting variable W3 gradually increases for producing a greater sound effect.

As described above, the vehicle 102 incorporates the noise/vibration/sound control ECU 100 according to the first embodiment shown in FIGS. 1 and 2 which comprises the ANC 16 for reducing noise in the vehicle cabin based on the engine rotation pulses Ep represented by the detected signal of vibrations of the engine 12, the AVC 50 for reducing vibrations of the vehicle 102 based on the engine rotation pulses Ep, and the ASC 60 for generating a sound effect in the vehicle 102 based on the engine rotation pulses Ep. The noise/vibration/sound control ECU 100 has the weighting variable calculator 110 serving as the coordination control means for selectively activating and inactivating the ANC 16, the AVC 50, and the ASC 60 or controlling their control characteristics in relation to each other, depending on the engine rotation frequency fe and the frequency change Δaf which correspond to the running state of the vehicle 102 detected by the engine rotation frequency detector 106 and the frequency change detector 108 which jointly serve as the running state detecting means 136.

Depending on the running state of the vehicle 102 detected by the running state detecting means 136, the weighting variable calculator 110 as the coordination control means selectively activates and inactivates the ANC 16, the AVC 50, and the ASC 60 or controls the control signals Da, Sp2, Sp3 representing their control characteristics in relation to each other. Consequently, the ANC 16, the AVC 50, and the ASC 60 are prevented from interfering with each other and hence the vehicle cabin environment of vibrations, noise, and sound is prevented from being impaired.

In the above embodiment, the vehicle 102 incorporates all of the three control apparatus, i.e., the ANC 16, the AVC 50, and the ASC 60. However, the principles of the present invention are also applicable to a vehicle incorporating at least two of the above three control apparatus.

In such a case, the function of the control apparatus which is not incorporated in the vehicle may be deleted from the noise/vibration/sound control ECU 100 or may not be performed, and the control apparatus inactivating and activating table 200 (excluding the control apparatus which is not incorporated) shown in FIG. 5 and the weighting variable maps MP1 through MP3 (excluding the weighting variable map relative to the control apparatus which is not incorporated) shown in FIG. 4 may be used to control the vehicle as with the vehicle 102 which incorporates all the three control apparatus.

Figure 6:
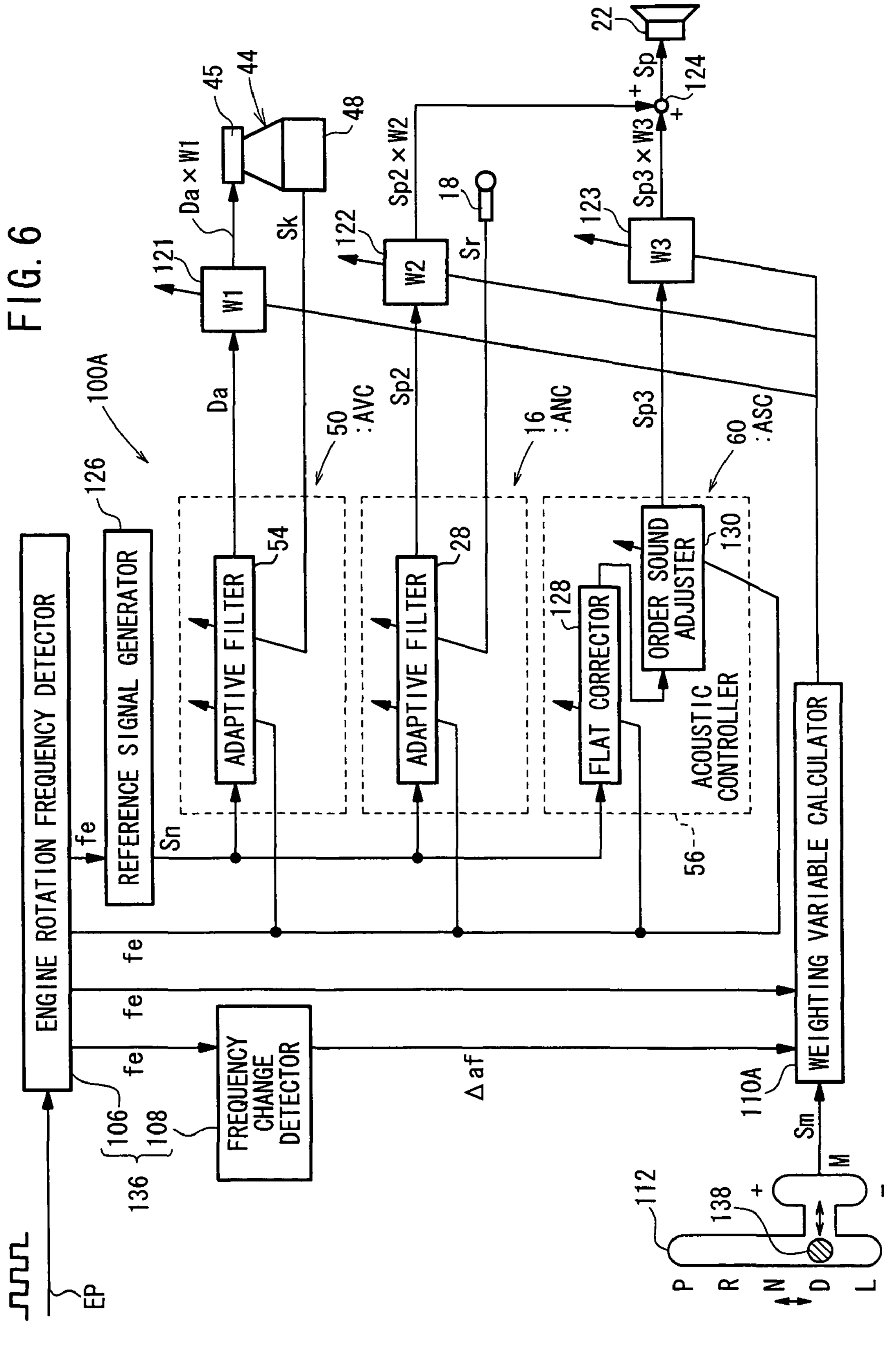
FIG. 6 is a block diagram of a noise/vibration/sound control ECU according to a second embodiment of the present invention.

FIG. 6 shows in block form a noise/vibration/sound control ECU 100A according to a second embodiment of the present invention.

As shown in FIG. 6, the noise/vibration/sound control ECU 100A differs from the noise/vibration/sound control ECU 100 according to the first embodiment in that the weighting variable calculator 110 as the coordination control means is replaced with a weighting variable calculator 110A, and the weighting variable calculator 110A is supplied from a transmission shifter 112 with a manual transmission mode signal Sm which is turned off when a CVT (Continuously Variable Transmission) mounted on the vehicle is in an automatic transmission mode and turned on when the CVT is in a manual transmission mode.

Figure 7:
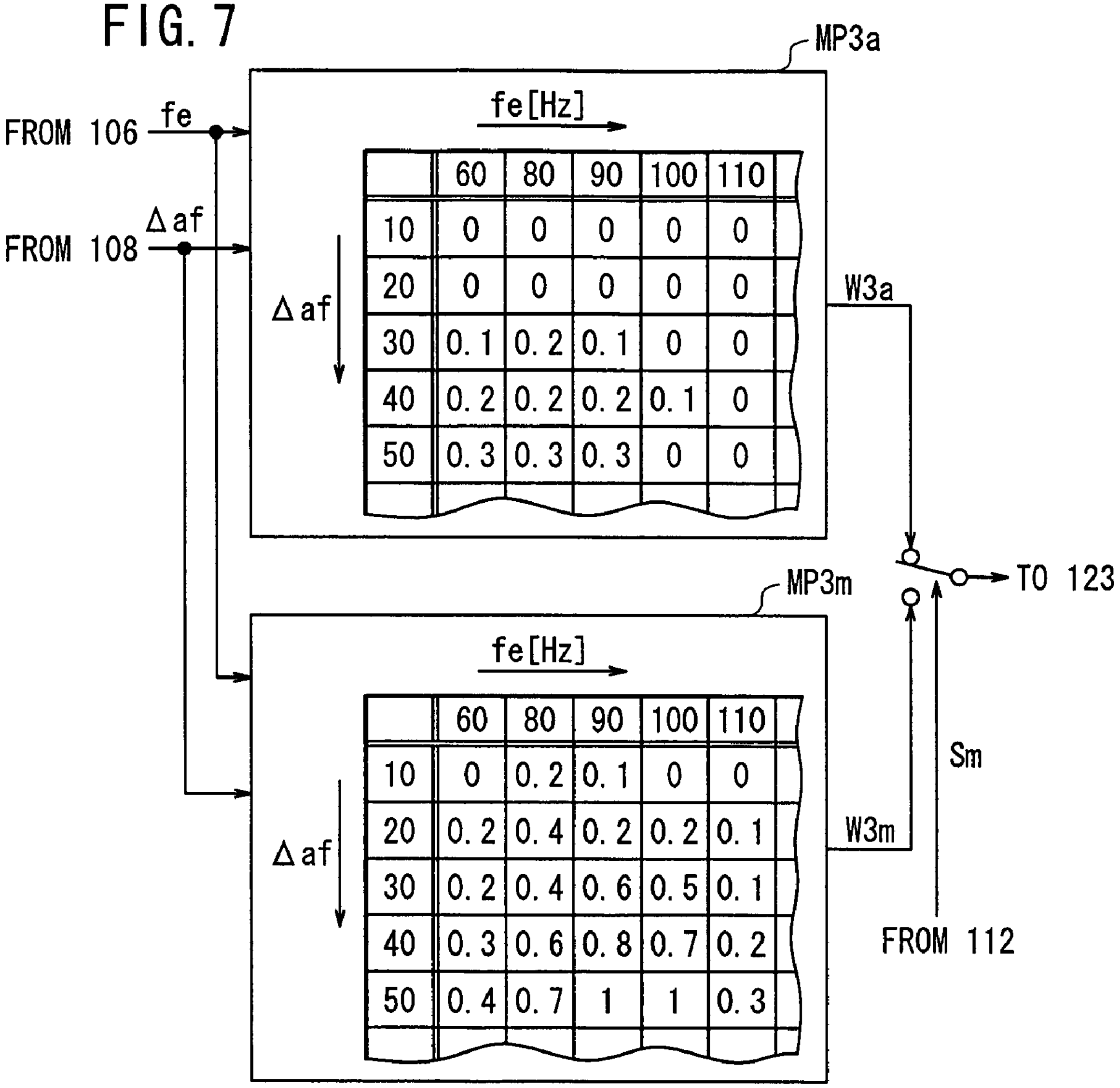
FIG. 7 is a diagram showing an ASC weighting variable map that is applied in an automatic transmission mode and an ASC weighting variable map that is applied in a manual transmission mode.

FIG. 7 shows by way of example a weighting variable map MP3*a* for the ASC 60 which is applicable in the automatic transmission mode and a weighting variable map MP3*m* for the ASC 60 which is applicable in the manual transmission mode, the weighting variable maps MP3*a*, MP3*m* being stored in a memory of the weighting variable calculator 110A. These weighting variable maps MP3*a*, MP3*m* are used in place of the weighting variable map MP3 for the ASC 60 which is shown in FIG. 4. In the noise/vibration/sound control ECU 10A, the memory of the weighting variable calculator 110A also stores the weighting variable map MP1 for the AVC 50 and the weighting variable map MP2 for the ANC 16 shown in FIG. 4.

The weighting variable calculator 110A of the noise/vibration/sound control ECU 100A calculates weighing variables W1, W2, W3 (W3*a* or W3*m*) to be set respectively in the weighting units 121, 122, 123 which are connected to the respective output terminals of the AVC 50, the ANC 16, the ASC 60, based on the engine rotation frequency fe, frequency change Δaf, and the manual transmission mode signal Sm from the transmission shifter 112.

The CVT basically comprises a drive pulley engaging the output shaft of the engine 12 and a driven pulley operatively coupled to the drive pulley through a steel belt. The drive and driven pulleys have respective slots in which the steel belt engages, and the widths of the slots are changed to relatively change the diameters of the torque transmission pitch circles for the steel belt to continuously change the transmission gear ratio of the CVT.

The shifter 112, which is coupled to the CVT, has a shift knob 138 that can selectively be brought into a parking position P, a reverse position R, a neutral position N, a drive position D for the CVT automatic transmission mode, and a low-gear drive position L. The shift knob 138 can also be brought from the drive position D into a manual transmission mode position M.

When the shift knob 138 is in the drive position D (CVT automatic transmission mode position), the CVT has its transmission gear ratio automatically variable continuously depending on the running state of the vehicle. When the shift knob 138 is in the manual transmission mode position M, the shift knob 138 can be manually moved in the positive or negative direction to change the transmission gear ratio through seven steps. The shifter 112 supplies a signal representing the manual transmission mode as the manual transmission mode signal Sm (which is turned on when the shift knob 138 is in the manual transmission mode position M and turned off in the other positions) to the weighting variable calculator 110A.

The noise/vibration/sound control ECU 100A according to the second embodiment operates as follows: In the automatic transmission mode when the manual transmission mode signal Sm is turned off, as can be seen from the weighing variable map MP3*a* that is applicable in the automatic transmission mode as shown in FIG. 7, when the frequency change Δaf is in a low range, the weighting variable W3*a* is set to 0 to inactivate the ASC 60 regardless of the engine rotation frequency fe, and as the frequency change Δaf is greater, the weighting variable W3*a* increases from 0 to operate the ASC 60 for thereby keeping quiet in the vehicle cabin while the driver is driving the vehicle 102.

In the manual transmission mode when the manual transmission mode signal Sm is turned on, as can be seen from the weighing variable map MP3*m*, as the engine rotation frequency fe increases from a low range to a high range and the frequency change Δaf increases from a low range to a high range, the weighting variable W3*m* gradually increases to operate the ASC 60. Since the ASC 60 is controlled to operate in almost all ranges except for an idling range, a sound effect is generated to give the driver or a passenger sporty feeling while driving the vehicle 102.

The present invention is not limited to the above embodiments. If the engine 12 is an engine having cylinders that can selectively be disabled, then the maps MP1, MP2, MP3, MP3*a*, MP3*m* may be changed to activate and inactivate the AVC 50, the ANC 16, the ASC 60 based on a cylinder disabling signal. Rotation pulses from the propeller shaft, rather than the engine rotation pulses Ep, may be used as the detected signal of vibrations of the engine.

Although certain preferred embodiments of the present invention have been shown and described in detail, it should be understood that various changes and modifications may be made therein without departing from the scope of the appended claims.

What is claimed is:

1. An active noise/sound control system for use in a vehicle, having an active noise control apparatus for reducing noise in a vehicle cabin based on a detected signal representative of engine vibrations, and an active sound control apparatus for generating a sound effect in the vehicle cabin based on said detected signal, said active noise control apparatus generating a reference signal based on said detected signal, generating a first control signal by changing an amplitude and a phase of the reference signal based on the detected signal picked up by a microphone positioned near an occupant of the vehicle, and supplying the first control signal to a speaker for radiating acoustic sounds to the occupant, said active sound control apparatus generating the reference signal based on said detected signal, generating a second control signal by changing an amplitude and a phase of the reference signal such that a sound effect depending on acceleration of the vehicle is produced, and supplying the second control signal to the speaker, said active noise/sound control system comprising:

running state detecting means for detecting a running state of the vehicle; and a weight setting means for setting weighting variables for the first control signal and the second control signal depending on the detected running state of the vehicle, wherein when detecting a running state as idling or cruising, the weight setting means sets the weighting variable for the first control signal greater than the weighting variable for the second control signal, and when detecting the running state as accelerating, the weight setting means sets the weighting variable for the second control signal greater than the weighting variable for the first control signal.

2. An active noise/sound control system according to claim 1, wherein said running state detecting means comprises:

an engine rotation frequency detector for detecting an engine rotation frequency; and a frequency change detector for detecting a frequency change in the detected engine rotation frequency; and wherein said weight setting means sets the weighting variables for control signals to be applied based on said engine rotation frequency and said frequency change.

3. An active noise/sound control system according to claim 2, wherein said vehicle has a transmission selectively operable in an automatic transmission mode and a manual transmission mode, and said weight setting means changes the weighting variables for the second control signal to be applied to said active sound control apparatus depending on whether said transmission operates in said automatic transmission mode or said manual transmission mode.

4. An active noise/sound control system according to claim 1, further comprising an active vibration control apparatus an active vibration control apparatus for reducing vibration, for reducing vibration, the active vibration control apparatus generating a reference signal based on said detected signal representative of the engine vibrations, generating a third control signal by changing an amplitude and a phase of the reference signal based on the detected signal detected by a vibration sensor positioned near a vibrating object, and supplying the third signal to an actuator positioned near the vibrating object, wherein when detecting a running state as idling, the weight setting means sets the weighting variables for the first control signal and the third control signal greater than the weighting variable for the second control signal, when detecting a running state as cruising, the weight setting means sets the weighting variable for the first control signal greater than the weighting variables for the second control signal and the third control signal, and when detecting the running state as accelerating, the weight setting means sets the weighting variable for the second control signal greater than the weighting variables for the first control signal and the third control signal.

5. A vehicle incorporating an active noise/sound control system having an active noise control apparatus for reducing noise in a vehicle cabin based on a detected signal representative of engine vibrations, and an active sound control apparatus for generating a sound effect in the vehicle cabin based on said detected signal, said active noise control apparatus generating a reference signal based on said detected signal, generating a first control signal by changing an amplitude and a phase of the reference signal based on the detected signal picked up by a microphone positioned near an occupant of the vehicle, and supplying the first control signal to a speaker for radiating acoustic sounds to the occupant, said active sound control apparatus generating the reference signal based on said detected signal, generating a second control signal by changing an amplitude and a phase of the reference signal such that a sound effect depending on acceleration of the vehicle is produced, and supplying the second control signal to the speaker, said vehicle comprising:

running state detecting means for detecting a running state of the vehicle; and a weight setting means for setting weighting variables for the first control signal and the second control signal depending on the detected running state of said vehicle, wherein when detecting a running state as idling or cruising, the weight setting means sets the weighting variable for the first control signal greater than the weighting variable for the second control signal, and when detecting the running state as accelerating, the weight setting means sets the weighting variable for the second control signal greater than the weighting variable for the first control signal.

6. A vehicle according to claim 5, wherein said running state detecting means comprises:

an engine rotation frequency detector for detecting an engine rotation frequency; and a frequency change detector for detecting a frequency change in the detected engine rotation frequency; and wherein said weight setting means sets the weighting variables for control signals to be applied based on said engine rotation frequency and said frequency change.

7. A vehicle according to claim 6, further comprising a transmission selectively operable in an automatic transmission mode and a manual transmission mode, wherein said weighting setting means changes the weighting variable for the second control signal to be applied to said active sound control apparatus depending on whether said transmission operates in said automatic transmission mode or said manual transmission mode.

8. A vehicle according to claim 5, wherein the active noise/sound control system further comprises an active vibration control apparatus an active vibration control apparatus for reducing vibration, for reducing vehicle vibration, the active vibration control apparatus generating a reference signal based on said detected signal representative of the engine vibrations, generating a third control signal by changing an amplitude and a phase of the reference signal based on the detected signal detected by a vibration sensor positioned near a vibrating object, and supplying the third signal to an actuator positioned near the vibrating object, wherein when detecting a running state as idling, the weight setting means sets the weighting variables for the first control signal and the third control signal greater than the weighting variable for the second control signal, when detecting a running state as cruising, the weight setting means sets the weighting variable for the first control signal greater than the weighting variables for the second control signal and the third control signal, and when detecting the running state as accelerating, the weight setting means sets the weighting variable for the second control signal greater than the weighting variables for the first control signal and the third control signal.

9. An active noise/vibration/sound control system for use in a vehicle, having at least two of an active noise control apparatus for reducing noise in a vehicle cabin based on a detected signal representative of engine vibrations, an active vibration control apparatus for reducing vehicle vibrations based on said detected signal, and an active sound control apparatus for generating a sound effect in the vehicle cabin based on said detected signal, said active noise/vibration/sound control system comprising:

running state detecting means for detecting a running state of the vehicle; and coordination control means for controlling activation and inactivation of said active noise control apparatus, said active vibration control apparatus, and said active sound control apparatus, or controlling control characteristics thereof or controlling control characteristics thereof in relation to each other, depending on the detected running state of the vehicle, wherein said running state detecting means comprises:

an engine rotation frequency detector for detecting an engine rotation frequency; and a frequency change detector for detecting a frequency change in the detected engine rotation frequency;

wherein said coordination control means comprises:

a weighting variable calculator for calculating weighting variables for control signals to be applied respectively to said active noise control apparatus, said active vibration control apparatus, and said active sound control apparatus, based on said engine rotation frequency and said frequency change; and wherein said vehicle has a transmission selectively operable in an automatic transmission mode and a manual transmission mode, and said weighting variable calculator changes weighting variables for the control signal to be applied to said active sound control apparatus depending on whether said transmission operates in said automatic transmission mode or said manual transmission mode.

10. A vehicle incorporating an active noise/vibration/sound control system having at least two of an active noise control apparatus for reducing noise in a vehicle cabin based on a detected signal representative of engine vibrations, an active vibration control apparatus for reducing vehicle vibrations based on said detected signal, and an active sound control apparatus for generating a sound effect in the vehicle cabin based on said detected signal, said vehicle comprising:

running state detecting means for detecting a running state of the vehicle; and coordination control means for controlling activation and inactivation of said active noise control apparatus, said active vibration control apparatus, and said active sound control apparatus, or controlling control characteristics thereof or controlling control characteristics thereof in relation to each other, depending on the detected running state of said vehicle, wherein said running state detecting means comprises:

an engine rotation frequency detector for detecting an engine rotation frequency; and a frequency change detector for detecting a frequency change in the detected engine rotation frequency;

wherein said coordination control means comprises:

a weighting variable calculator for calculating weighting variables for control signals to be applied respectively to said active noise control apparatus, said active vibration control apparatus, and said active sound control apparatus, based on said engine rotation frequency and said frequency change; and wherein said vehicle has a transmission selectively operable in an automatic transmission mode and a manual transmission mode, wherein said weighting calculator changes weighting variables for the control signal to be applied to said active sound control apparatus depending on whether said transmission operates in said automatic transmission mode or said manual transmission mode.

* * * * *